(12) United States Patent
Mangiagalli

(10) Patent No.: US 11,975,464 B2
(45) Date of Patent: May 7, 2024

(54) MANUFACTURING A TWO-PART ELASTOMERIC PLUNGER

(71) Applicant: SANOFI, Paris (FR)

(72) Inventor: Paolo Mangiagalli, Paris (FR)

(73) Assignee: Sanofi, Paris (FR)

(*) Notice: Subject to any disclaimer, the term of this patent is extended or adjusted under 35 U.S.C. 154(b) by 996 days.

(21) Appl. No.: 16/954,335

(22) PCT Filed: Dec. 14, 2018

(86) PCT No.: PCT/EP2018/084869
§ 371 (c)(1),
(2) Date: Jun. 16, 2020

(87) PCT Pub. No.: WO2019/121358
PCT Pub. Date: Jun. 27, 2019

(65) Prior Publication Data
US 2021/0078213 A1 Mar. 18, 2021

(30) Foreign Application Priority Data
Dec. 18, 2017 (EP) .................................. 17306804

(51) Int. Cl.
*B29C 43/18* (2006.01)
*A61M 5/142* (2006.01)
(Continued)

(52) U.S. Cl.
CPC .............. *B29C 43/18* (2013.01); *A61M 5/142* (2013.01); *A61M 5/20* (2013.01);
(Continued)

(58) Field of Classification Search
CPC ... B29C 43/18; B29C 35/0805; B29C 43/305; B29C 43/34; B29C 2035/0827;
(Continued)

(56) References Cited

U.S. PATENT DOCUMENTS

2001/0023275 A1* 9/2001 Tsuji .................. C08L 83/04
525/100
2001/0034506 A1 10/2001 Hirschman et al.
(Continued)

FOREIGN PATENT DOCUMENTS

JP 2007-532181 11/2007
WO WO 2005/099793 10/2005
(Continued)

OTHER PUBLICATIONS

PCT International Preliminary Report on Patentability in International Appln. No. PCT/EP2018/084869, dated Jun. 23, 2020, 8 pages.
(Continued)

*Primary Examiner* — S. Behrooz Ghorishi
(74) *Attorney, Agent, or Firm* — Fish & Richardson P.C.

(57) ABSTRACT

A technique of manufacturing an elastomeric container closure or plunger with embedded functional components to avoid thermal damage to the components is described. The technique includes molding a drug-contacting part from a first material at a first temperature and for a first length of time defining a first thermal exposure; after molding the drug-contacting part, inserting ancillary components into the drug-contacting part, where the ancillary components have an operational thermal budget less than the first thermal exposure; and overmolding the drug-contracting part and the ancillary components with a second material at a second temperature for a second length of time to form a non-drug-contacting part that mechanically connects the non-drug-contacting part and the drug-contacting part to form the elastomeric container closure and seals the ancillary components inside the elastomeric container closure. The overmolding defines a thermal exposure less than the operational thermal budget of the ancillary components.

21 Claims, 12 Drawing Sheets

(51) Int. Cl.
  *A61M 5/20* (2006.01)
  *A61M 5/315* (2006.01)
  *A61M 5/32* (2006.01)
  *B29C 35/08* (2006.01)
  *B29C 43/30* (2006.01)
  *B29C 43/34* (2006.01)
  *B29K 23/00* (2006.01)
  *B29K 83/00* (2006.01)

(52) U.S. Cl.
  CPC .......... *A61M 5/31511* (2013.01); *A61M 5/32* (2013.01); *B29C 35/0805* (2013.01); *B29C 43/305* (2013.01); *B29C 43/34* (2013.01); A61M 2205/0216 (2013.01); A61M 2205/0238 (2013.01); A61M 2207/00 (2013.01); A61M 2207/10 (2013.01); B29C 2035/0827 (2013.01); B29C 2043/182 (2013.01); B29K 2023/22 (2013.01); B29K 2083/005 (2013.01)

(58) Field of Classification Search
  CPC ... B29C 2043/182; A61M 5/142; A61M 5/20; A61M 5/31511; A61M 5/32; A61M 2205/0216; A61M 2205/0238; A61M 2207/00; A61M 2207/10; A61M 2205/3306; A61M 2205/3327; B29K 2023/22; B29K 2083/005
  See application file for complete search history.

(56) References Cited

U.S. PATENT DOCUMENTS

| | | |
|---|---|---|
| 2014/0303567 A1 | 10/2014 | Qurishi et al. |
| 2015/0217059 A1 | 8/2015 | Ashby et al. |
| 2017/0316177 A1* | 11/2017 | Mirov .................. A61M 5/315 |
| 2020/0041543 A1* | 2/2020 | Maeda .................. C01B 32/162 |
| 2023/0045058 A1* | 2/2023 | Drake .................... B29C 43/18 |

FOREIGN PATENT DOCUMENTS

| | | |
|---|---|---|
| WO | WO 2010/133676 | 11/2010 |
| WO | WO 2011/032956 | 3/2011 |
| WO | WO 2013/064590 | 5/2013 |
| WO | WO 2016/113409 | 7/2016 |

OTHER PUBLICATIONS

PCT International Search Report and Written Opinion in International Appln. No. PCT/EP2018/084869, dated Feb. 12, 2019, 11 pages.

* cited by examiner

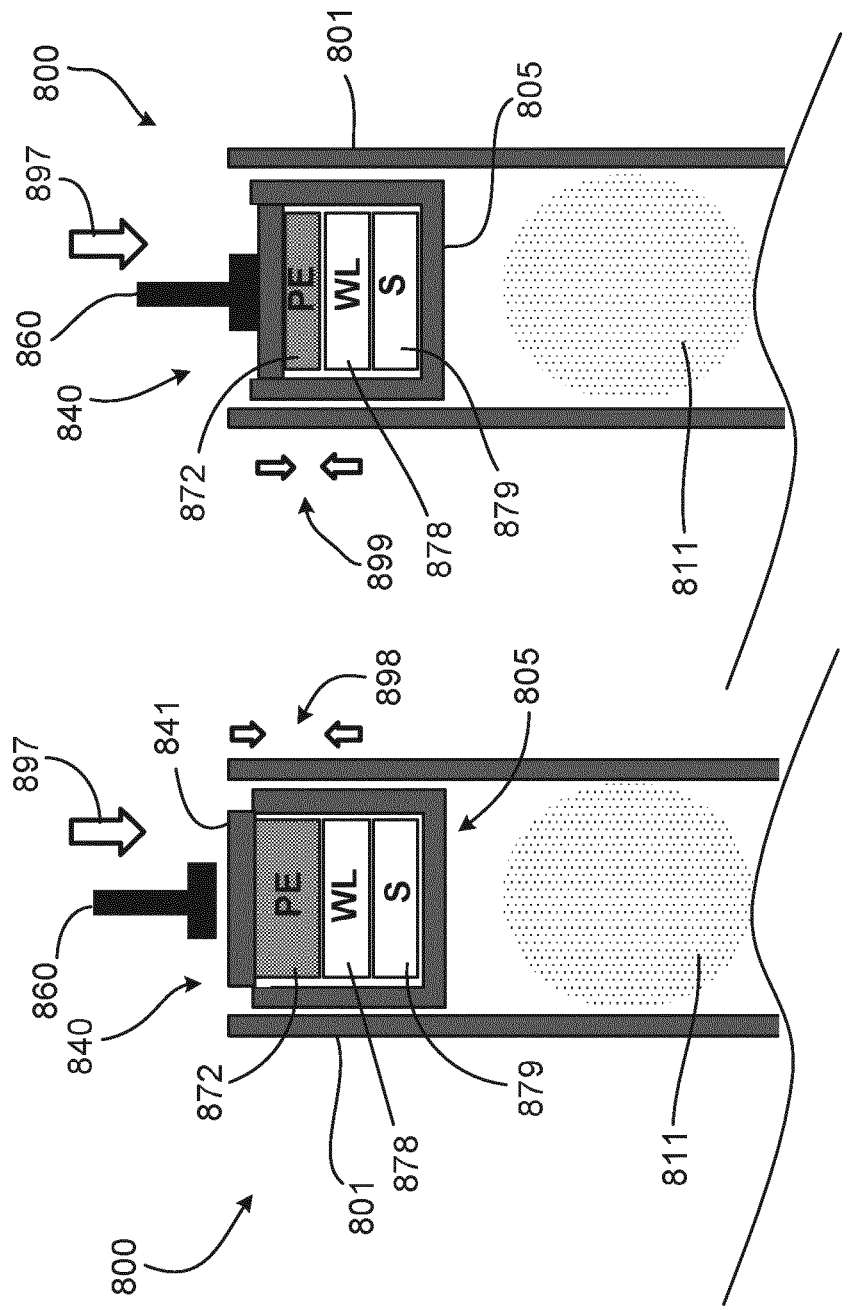

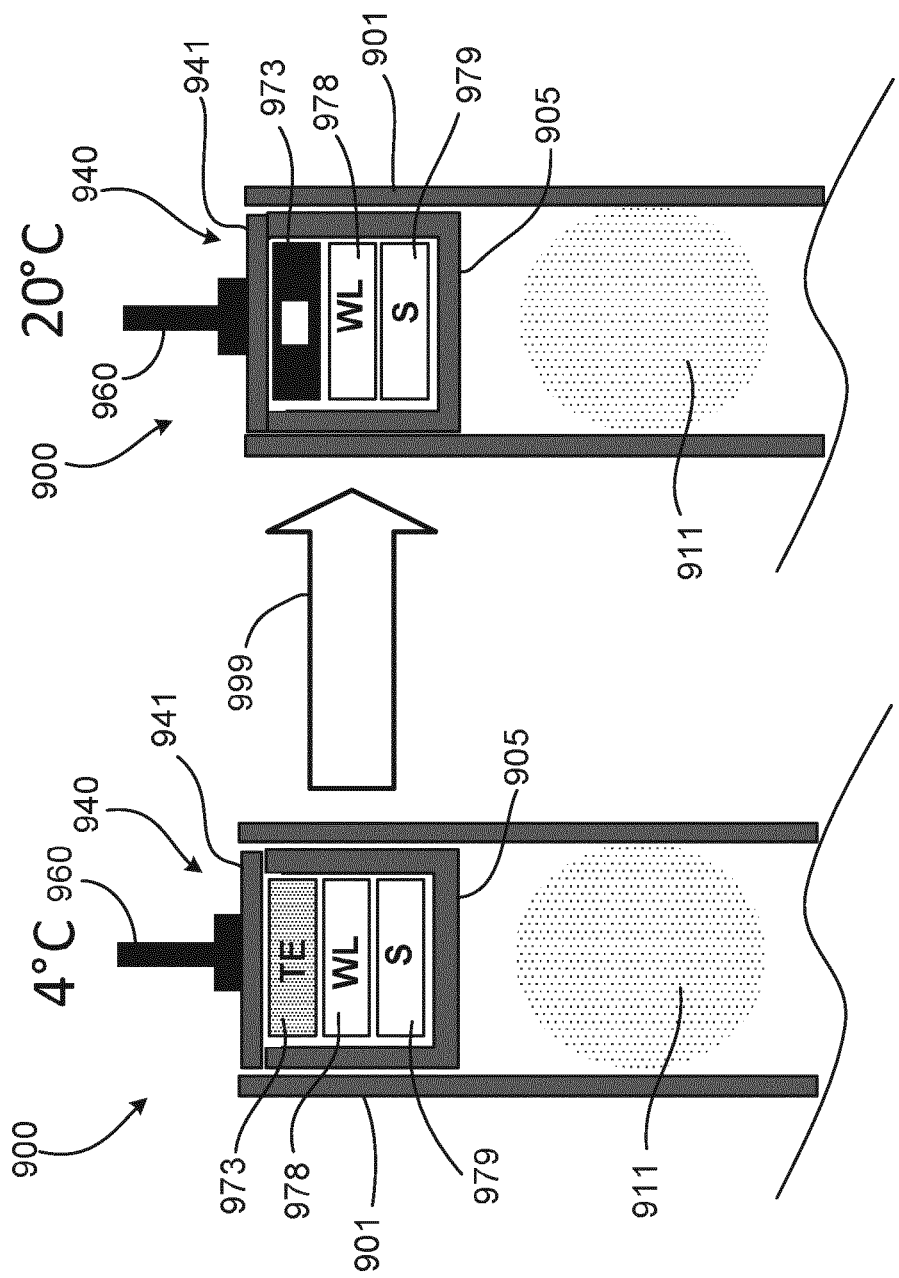

MANUFACTURING A TWO-PART ELASTOMERIC PLUNGER

CROSS REFERENCE TO RELATED APPLICATIONS

The present application is the national stage entry of International Patent Application No. PCT/EP2018/084869, filed on Dec. 14, 2018, and claims priority to Application No. EP 17306804.0, filed on Dec. 18, 2017, the disclosures of which are incorporated herein by reference.

TECHNICAL FIELD

This description relates to manufacturing an elastomeric plunger with internal electronic components for use in a cartridge or syringe of an injection device configured to eject a medicament using the plunger.

BACKGROUND

A variety of diseases exist that require treatment by injection of a medicament. Such injection can be performed using injection devices, which are applied either by medical personnel or by patients themselves. As an example, type-1 and type-2 diabetes can be treated by patients themselves by injection of insulin doses, for example once or several times per day. For instance, a pre-filled disposable insulin pen or autoinjector can be used as an injection device. Alternatively, a re-usable pen or autoinjector may be used. A re-usable pen or autoinjector allows replacement of an empty medicament cartridge by a new one. Each of these devices typically employ an elastomeric plunger or bung to drive a medicament from the cartridge or a syringe in the device and some include one or more electronic devices embedded in the plunger.

SUMMARY

An example implementation is a method of manufacturing an elastomeric container closure with embedded functional components. The method includes molding a drug-contacting part of the elastomeric container closure from a first material at a first temperature and for a first length of time, the exposure to the first temperature for the first length of time defining a first thermal exposure. After the molding the drug-contacting part, inserting ancillary components into the drug-contacting part, the ancillary components having an operational thermal budget less than the first thermal exposure, and overmolding the drug-contracting part and the inserted ancillary components with a second material at a second temperature for a second length of time to form a non-drug-contacting part and mechanically connect the non-drug-contacting part and the drug-contacting part to form the elastomeric container closure and seal the ancillary components inside the elastomeric container closure. The overmolding defines a second thermal exposure that is less than the operational thermal budget of the ancillary components.

In some instances, the ancillary components are configured to operate after exposure to temperatures lower than the first temperature of the first material during the molding step.

In some instances, the second temperature is lower than the first temperature, and where the ancillary components are configured to operate after exposure to the second temperature of the second material during the overmolding step.

In some instances, the ancillary components are incompatible with the first temperature of the molding of the drug-contacting part.

In some instances, the ancillary components comprise functional electronic components.

In some instances, the overmolding includes a UV curing process of the second material.

In some instances, the first temperature is between 150° C. and 180° C.

In some instances, the second temperature is between 150° C. and 120° C.

In some instances, the second temperature is lower than 120° C.

In some instances, the second temperature is lower than 80° C.

In some instances, the second temperature is lower than 45° C.

In some instances, the first material comprises halobutyls.

In some instances, the method includes, prior to the insert of the ancillary components, laminating the drug-contacting part with a fluoropolymer film prior to the insert of the ancillary components.

In some instances, the first material comprises pharmaceutical-grade thermosets selected from the group comprising: halobutyls, polyisoprenes, and styrene-butadiene, and the molding of the drug-contacting part includes compression molding.

In some instances, the first material comprises thermoplastic elastomers, and the molding of the drug-contacting part includes injection molding.

In some instances, the second material comprises silicone rubber.

In some instances, the second material comprises at least one of liquid silicone rubber and high consistency silicone rubber.

In some instances, the first material is gas impermeable.

In some instances, the method includes trimming the molded drug-contacting part after insertion of the ancillary components.

In some instances, the method includes trimming the molded drug-contacting part before insertion of the ancillary components.

In some instances, the elastomeric container closure defines a plunger or stopper configured to be inserted into a syringe housing, a cartridge housing, or a medicament container.

In some instances, the method includes, after the closing, sterilizing the elastomeric container closure with a sterilization process having a thermal budget less than the thermal budget of the ancillary components.

In some instances, the molding includes molding the drug-contacting part in a first mold and wherein the overmolding includes overmolding the drug-contacting part and the ancillary components in a second mold, and the method includes removing the drug-contacting part from the first mold and disposing the drug-contacting part into the second mold.

In some instances, the ancillary components are insert into the drug-contacting part prior to the removal of the drug-contacting part from the first mold.

In some instances, the ancillary components are insert into the drug-contacting part after the drug-contacting part is disposed in the second mold.

In some instances, the ancillary components include a battery.

In some instances, the drug-contacting part defines a receptacle for receiving the ancillary components.

In some instances, the drug-contacting part defines a protrusion configured to extend into the overmolded non-drug-contacting part in order to increase mechanical adhesion between the drug-contacting part and the non-drug-contacting part after the overmolding of the non-drug-contacting part around the protrusion.

In some instances, the protrusion defines one or more of: a thread, a flange, and an embossment.

In some instances the flange is configured to increase the mechanical adhesion of the drug-contacting part to the overmolded non-drug-contacting part.

Another example of the present disclosure is an elastomeric container closure manufactured according to the method, described above, of molding a drug-contacting part of the elastomeric container closure from a first material at a first temperature and for a first length of time, the exposure to the first temperature for the first length of time defining a first thermal exposure. After the molding the drug-contacting part, inserting ancillary components into the drug-contacting part, the ancillary components having an operational thermal budget less than the first thermal exposure, and overmolding the drug-contracting part and the inserted ancillary components with a second material at a second temperature for a second length of time to form a non-drug-contacting part and mechanically connect the non-drug-contacting part and the drug-contacting part to form the elastomeric container closure and seal the ancillary components inside the elastomeric container closure. The overmolding defines a second thermal exposure that is less than the operational thermal budget of the ancillary components.

Yet another example is a drug delivery device including the elastomeric container closure manufactured according to the methods described herein.

In some instances, the drug delivery device includes a container having an open end sealed by the elastomeric container closure, and the container comprising a medicament.

In some instances, the medicament includes a pharmaceutically active compound.

In general, the examples described herein relate to a manufacturing technique for pharmaceutical elastomeric closures components with embedded functional components. The techniques and related components described herein constitute an efficient manner of manufacturing container closure components (i.e., plungers with validated pharmaceutical rubbers) with embedded components that enhance the functionality beyond pure containment. In some instances, the embedded components are electronic active components for sensing and monitoring, or passive components for tracking and tracing the operation of the device and/or the administration of a medicament from the device.

BRIEF DESCRIPTION OF FIGURES

FIGS. 8A and 8B are cross-sectional views of a plunger disposed within a cartridge and powered by a piezoelectric system.

FIGS. 9A and 9B are cross-sectional views of a plunger disposed within a cartridge and powered by a thermoelectric system.

DETAILED DESCRIPTION

Figure 1:
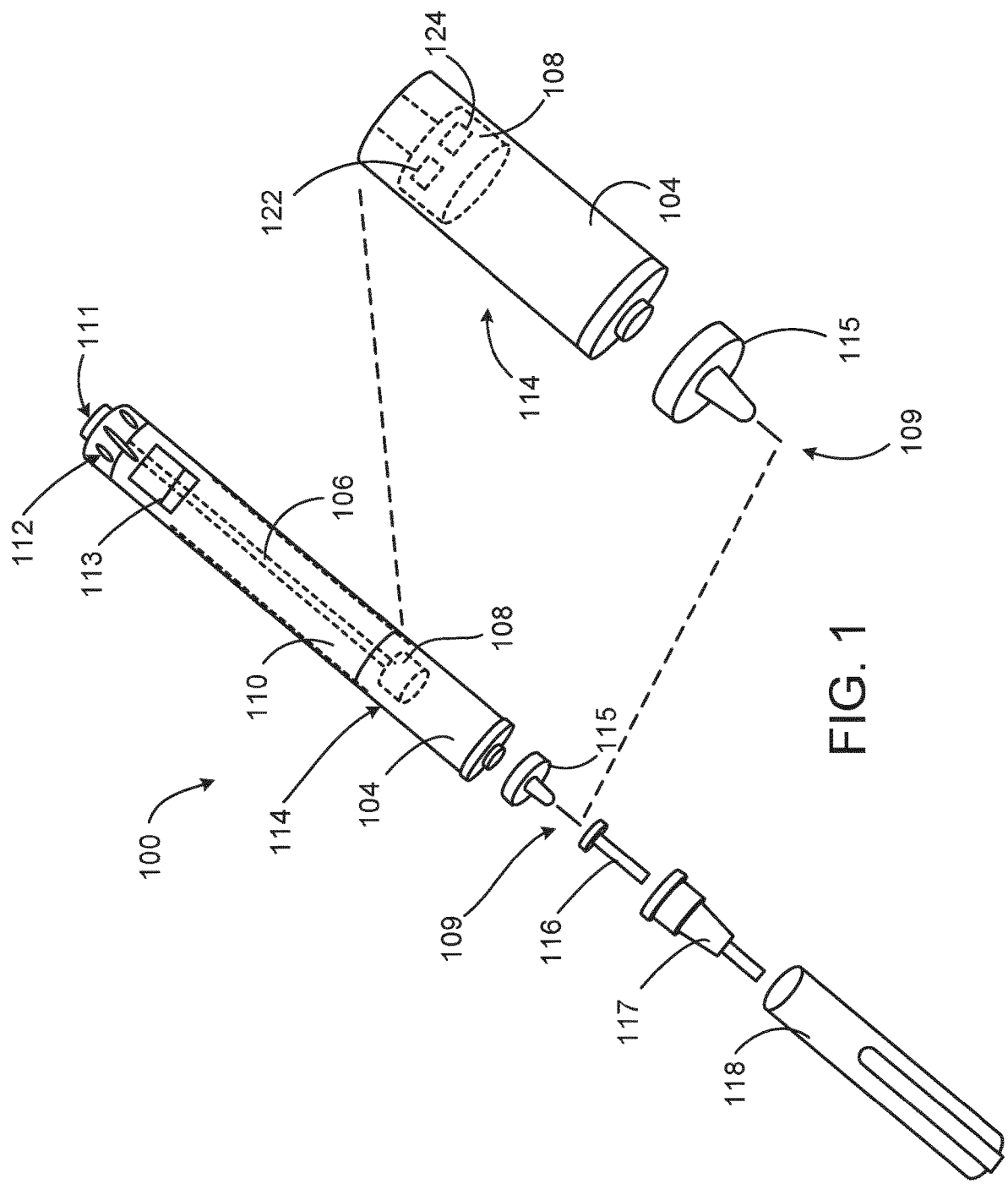
FIG. 1 is an exploded view of an injection device.

Some cartridge-based injection and medical syringe systems are difficult to manufacture if they include electronics in the replaceable portions of the device (e.g., a cartridge stopper or a cartridge housing) that may be unable to survive the heating of the molding process of a cartridge plunger. In some examples, the cartridge plunger (e.g., stopper or bung) can be manufactured using a two-step process, where a drug-contacting part of the plunger is molded prior to the insertion of some ancillary electronic components into the drug-contacting part, after which, a second molding around the drug-contacting part and the ancillary components completes the plunger. For example, a first molding process of a drug-contacting part of a plunger is done using a first material suitable for sealing a drug inside a cartridge, but at a thermal exposure (i.e., a length of exposure of the first material to a temperature during the molding) that may harm or destroy a set of ancillary electronic components to be included in the completed stopper. Next, after the molding of the drug-contacting part is completed, ancillary electronic components are inserted into the drug-contacting part and a second overmolding of the two part is done using a second material to form a non-drug-contacting part of the plunger. The second material is overmolded over the ancillary electronic components at a thermal exposure that the ancillary electronic components are able to survive, by either being done at a temperature below a maximum temperature limit of the ancillary electronic components or by exposing the ancillary electronic components to temperature above their maximum temperature limit, but for a time sufficient to maintain the ancillary electronic components below their thermal budget (i.e., a function of temperature and time).

Also in some instances, the drug-contacting part of the plunger or stopper is constructed to seal against the cartridge wall with soft O-ring seals, therefore without the second material of the non-drug contacting part contacting the sterilized liquid inside the cartridge. In this manner, the drug-contacting part of the plunger seals the cartridge, and the non-drug-contacting part of the plunger can receive a plunger rod to drive the plunger into the cartridge.

In general, the examples described herein relate to a manufacturing technique for pharmaceutical elastomeric closures components with embedded functional components. The techniques and related components described herein constitute an efficient manner of manufacturing container closure components (i.e., plungers with validated pharmaceutical rubbers) with embedded components that enhance the functionality beyond pure containment. In some instances, the embedded components are electronic active components for sensing and monitoring, or passive components for tracking and tracing the operation of the device and/or the administration of a medicament from the device.

Traditional high-volume rubber pharmaceutical closures are manufactured using a single material compression molding of a thermoset-elastomers or injection molding of thermoplastic or thermoset-elastomers. Often, the thermal budget (i.e., thermal exposure) associated with those processes is incompatible with ancillary components that could be embedded in plunger to enable additional functionality of the plunger.

Examples of the two-step manufacturing process presently described enable embedding ancillary components into a container plunger where the ancillary components are unable to survive exposure to the molding process of the drug-contacting part of the plunger.

FIG. 1 is an exploded view of an injection device 100. The injection device 100 includes a housing 110 and a having therein a cartridge 114 with cartridge housing 104, to which a needle assembly 115 can be affixed. The needle 109 of needle assembly 115 is protected by an inner needle cap 116 and an outer needle cap 117, which in turn can be covered by cap 118. A medicament or drug dose to be ejected from the injection device 100 is selected by turning a dosage knob 112, and the selected dose is displayed via a dosage window or display 113, for instance in multiples of so-called International Units (IU), where, for example, one IU is the biological equivalent of about 45.5 micrograms of pure crystalline insulin (1/22 mg). An example of a selected dose displayed in dosage window or display 113 may for instance be 30 IUs, as shown in FIG. 1. The selected dose may equally well be displayed differently, for instance by an electronic display. The dosage window 113 relates to the section of the injection device through or on which the selected dosage is visible.

As described further below, the injection device 100 may include one or more ancillary electronic components 122, 124, some of which may be included in the plunger 108, for example.

Turning the dosage knob 112 causes a mechanical click sound to provide acoustical feedback to a user. The numbers displayed in the dosage display 113 are printed on a sleeve that is contained in the housing 110 and mechanically interacts with a piston in the cartridge 114. When the needle 115 is stuck into a skin portion of a patient, and then the injection button 111 is pushed, the drug dose (e.g., insulin) displayed in the dosage window 113 will be ejected from the injection device 100. During an injection, a drive mechanism 106, which is shown as an outline of a plunger arm, drives a stopper (also referred to interchangeably herein as a plunger) 108 into the cartridge (e.g., cartridge 114). When the needle 115 of injection device 100 remains for a certain time in the skin portion after the injection button 111 is pushed, a high percentage of the dose is actually injected into the patient's body. Ejection of the insulin dose also causes a mechanical click sound, which is however different from the sounds produced when using the dosage knob 112.

The injection device 100 may be used for several injection processes until either insulin cartridge 114 is empty or the expiration date of injection device 100 (e.g. 28 days after the first use) is reached.

Furthermore, before using injection device 100 for the first time, it may be useful to perform a so-called "prime shot" to remove air from insulin cartridge 114 and needle 109, for instance by selecting two units of insulin and pressing injection button 111 while holding injection device 100 with the needle 109 upwards.

For simplicity of presentation, in the following, it will be exemplarily assumed that the ejected doses substantially correspond to the injected doses, so that, for instance when making a proposal for a dose to be injected next, this dose equals the dose that has to ejected by the injection device. Nevertheless, differences (e.g. losses) between the ejected doses and the injected doses may of course be taken into account.

Figure 2A:
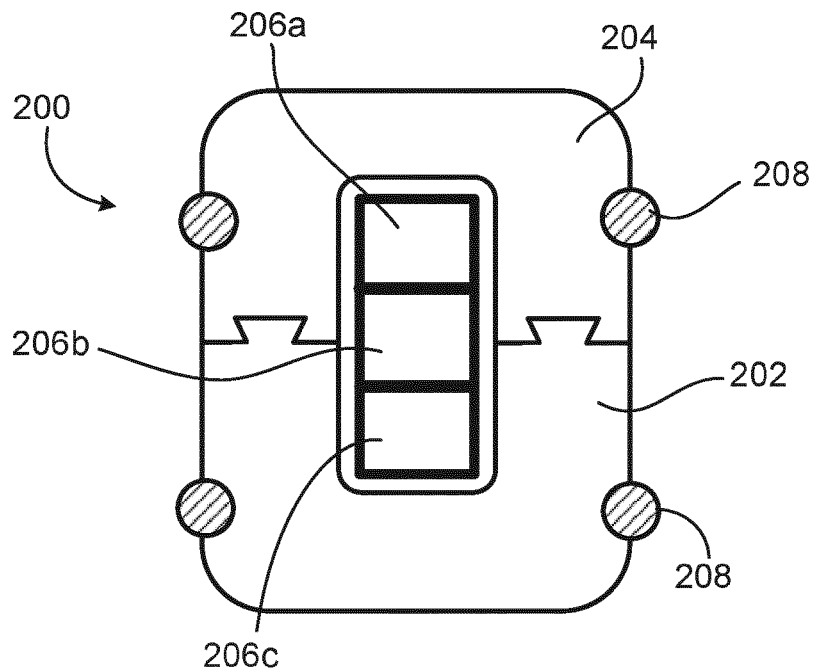
FIG. 2A is a cross sectional view of a plunger configured to be disposed in an injection device, the plunger having a drug-contacting part and a non-drug-contacting part with electronic devices embedded in the non-drug-contacting part.

FIG. 2A is a cross sectional view of an implementation of a plunger 200 configured to be disposed in an injection device (e.g., the injection device 100), the plunger 200 having a drug-contacting part 202 and a non-drug-contacting part 204 with electronic devices embedded in the non-drug-contacting part 204. In some instances, the electronic devices are sealed in the plunger 200 by the non-drug-contacting part 204. FIG. 2A illustrates the plunger 200 includes the drug-contacting part 202 and the non-drug-contacting part 204 containing electronic devices 206a, 206b, and 206c, which, in some instances, are sealed against the non-drug-contacting part 204 by the material of the non-drug-contacting part 204 during an overmolding process after the molding of the drug-contacting part 202. In this implementation, the non-drug-contacting part 204 in configured to be overmolded around the drug-contacting part 202 during manufacturing and after insertion of the electronic devices 206a, 206b, and 206c. In some instances, the drug-contracting part 202 is manufactured using a first molding step and the electronic devices 206a, 206b, and 206c are inserted into the drug-contacting part 202 after the first molding step. Subsequently, in a second molding step, the non-drug-contacting part 204 is molded against the drug contacting part 202 to seal the electronic devices 206a, 206b, and 206c into the plunger 200. Together the drug-contacting part 202 and the non-drug-contacting part 204 seal the embedded electronic devices 206a, 206b, and 206c into the plunger 200. In some instances, the electronic devices 206a, 206b, and 206c are held in place by the drug-contacting part 202 (e.g., inserted into a cavity) prior to the second molding of the non-drug-contacting part 204. In some instances, the drug-contacting part 202 includes sealing elements 208 (e.g. an O-ring) that are arranged to provide a sealing interface with an inner surface of the cartridge 104 when the drug-contacting part 202 is inserted into the cartridge 114. In some instances, the sealing elements 208 are integrated into the drug-contacting part 202 as sealing protrusions.

The materials selected for the drug-contacting part 202 and the non-drug-contacting part 204 are selected based on their hardness, elasticity, and their heat resistive or insulating properties. In some instances, the non-drug-contacting part is constructed from a material chosen to be able to be molded at a temperature below the maximum exposure temperature of the embedded electronic devices 206a, 206b, and 206c, or a material able to be molded for a temperature and time able to maintain the embedded electronic devices 206a, 206b, and 206c below a minimum thermal budget of the electronic devices 206a, 206b, and 206c. In some implementations, the drug-contacting part 202 and the non-drug-contacting part 204 are made of polymer materials with varying elastic properties. In some implementations, heat resistive coatings may also be applied to the non-drugcontacting part 204 or to the drug-contacting part 202 to increase heat resistance, such as, for example, a polytetrafluoroethylene (PTFE) coating. In some cases, the drug-contacting part 202 is made of material, which is selected to be compatible with the medicament, e.g. PP, PE, COC, COP, PTFE or butyl rubber at the surface 203 which is in contact with the medicament.

The embedded electronic devices 206a, 206b, and 206c may include, for example, a sensor, an energy source, a microcontroller, and a wireless transceiver. The sensor may be, in some instances, a sensor/transmitter device such as, for example, a piezoelectric device, an acoustic sensor, or an electromagnetic sensor. The sensor/transmitter may transmit a signal, such as, for example, an ultrasonic, acoustic, light, or other signal through the plunger 200 and measure a response which may, in some instances, be used to determine the position of the plunger 200 in a cartridge 114 or if an injection of the syringe has occurred. In some instances, the response received by the sensor is provided to a controller (e.g. an embedded or an external microcontroller) which may receive the response and calculate a state of the cartridge 114. The state of the cartridge 114 may correspond to, in some instances, a fill level of medicament in the cartridge 114 or a position of the plunger 200. In some instances, the state of the cartridge 114 enables a measurement of an injected dose of medicament.

In some instances, the energy source is a battery a battery, by any energy harvesting technologies, which may load a capacitor or a solar source. The wireless transceiver may communicate with an external electronic device as well as with the sensor and energy source. The external electronic device, which may be the controller, may communicate data received from the sensor to an external database. The wireless transceiver may communicate using any known wireless communication technique including, for example Bluetooth, NFC, or radio frequencies.

Figure 2B:
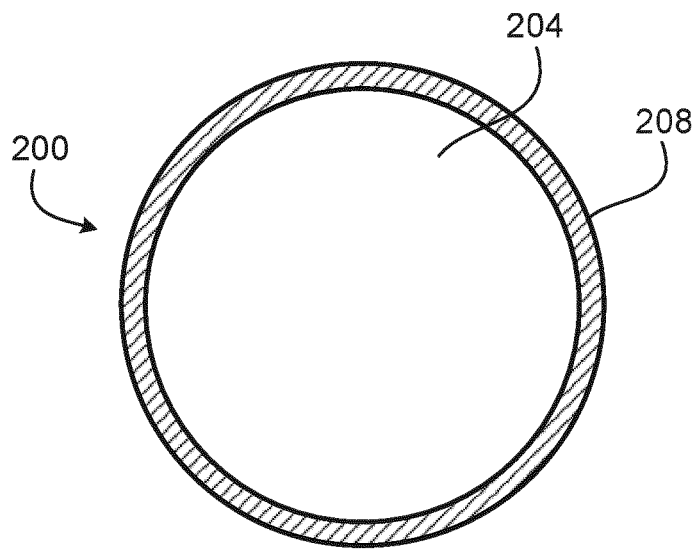
FIG. 2B is a top view of the plunger of FIG. 2A.

FIG. 2B is a top view of the plunger 200 of FIG. 2A. Drug-contacting part 202 surrounds non-drug-contacting part 204 and interfaces with sealing element 208, which forms a sealing interface with the cartridge 114 upon the plunger's 200 introduction into the cartridge 114. The sealing interface may form at least part of a sterile barrier within the cartridge 114, which is required to preserve the sterility of the medicament to be delivered by the injection device.

Figure 3A:
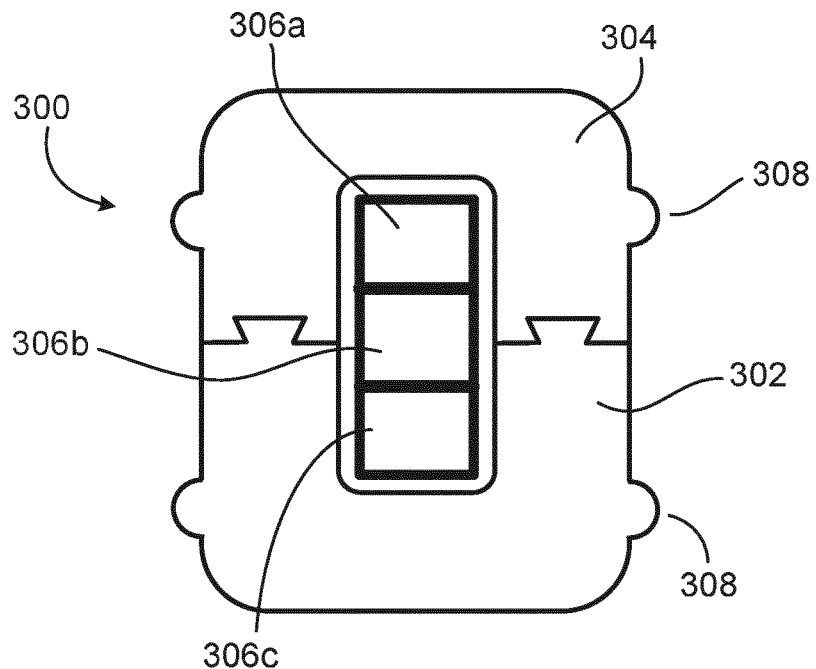
FIG. 3A is a cross sectional view of a plunger configured to be disposed in an injection device, the plunger having a drug-contacting part and a non-drug-contacting part with electronic devices embedded in the non-drug-contacting part.

FIG. 3A is a cross sectional view of a plunger 300 configured to be disposed in an injection device 100, the plunger 300 having a drug-contacting part 302 and a non-drug-contacting part 304 with embedded electronic devices 306a, 306b, 306c. In some instances, the drug-contacting part 302 and the non-drug-contacting part 304 are substantially inseparable after the overmolding of the non-drug-contacting part. For example, the non-drug-contacting part 304 may be molded around protrusions of the drug-contacting part 302 or secured using an adhesive to bond the non-drug-contacting part 304 and the drug-contacting part 302 together. The non-drug-contacting part 304 contains embedded electronic devices 306a, 306b, and 306c. In one implementation, after the molding of the drug-contacting part 302 from a first material, the electronic devices 306a, 306b, and 306c are inserted into the drug-contacting part 302 and a second material is molded around electronic devices 306a, 306b, and 306c to form the non-drug-contacting part 304. In another implementation, the electronic devices 306a, 306b, 306c may be introduced into the second material while it is in an uncured, softened state before the second material solidifies to form the non-drug-contacting part 304. The integrated sealing element 308 is configured to provide a sealing interface with the cartridge 114 upon inserting the plunger 300 the cartridge 114.

The various materials from which the drug-contacting part 302 and the non-drug-contacting part 304 could be produced as well as the various electronic devices that may be embedded in the non-drug-contacting part are described above with respect to FIG. 2A. Additionally, the material for the drug-contacting part 302 may be medical grade with the plunger drug-contacting part 302 being configured to come in contact with the medicament.

Figure 3B:
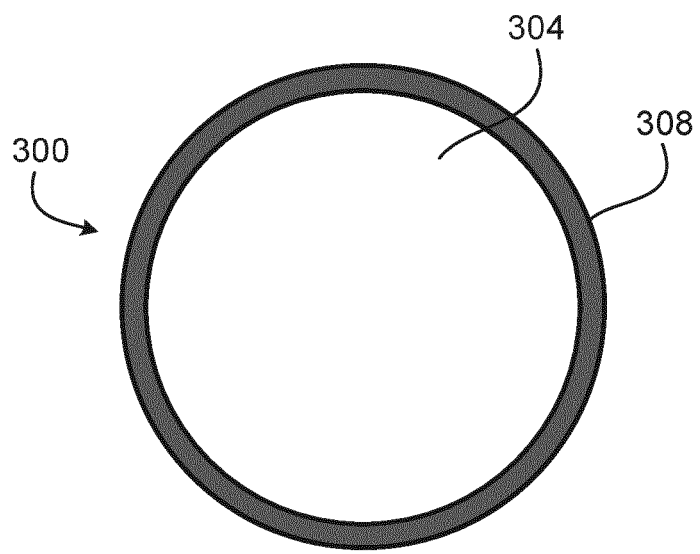
FIG. 3B is a top view of the plunger of FIG. 3A.

FIG. 3B is a top view of the plunger of FIG. 3A. Drug-contacting part 302 surrounds non-drug-contacting part 304 and includes an integrated sealing element 308, which forms a sealing interface with the cartridge 114 upon the plunger's 300 introduction into the cartridge 114. The sealing interface may form at least part of a sterile barrier within the cartridge 114, which is required to preserve the sterility of the medicament to be delivered by the injection device 100.

Figure 3C:
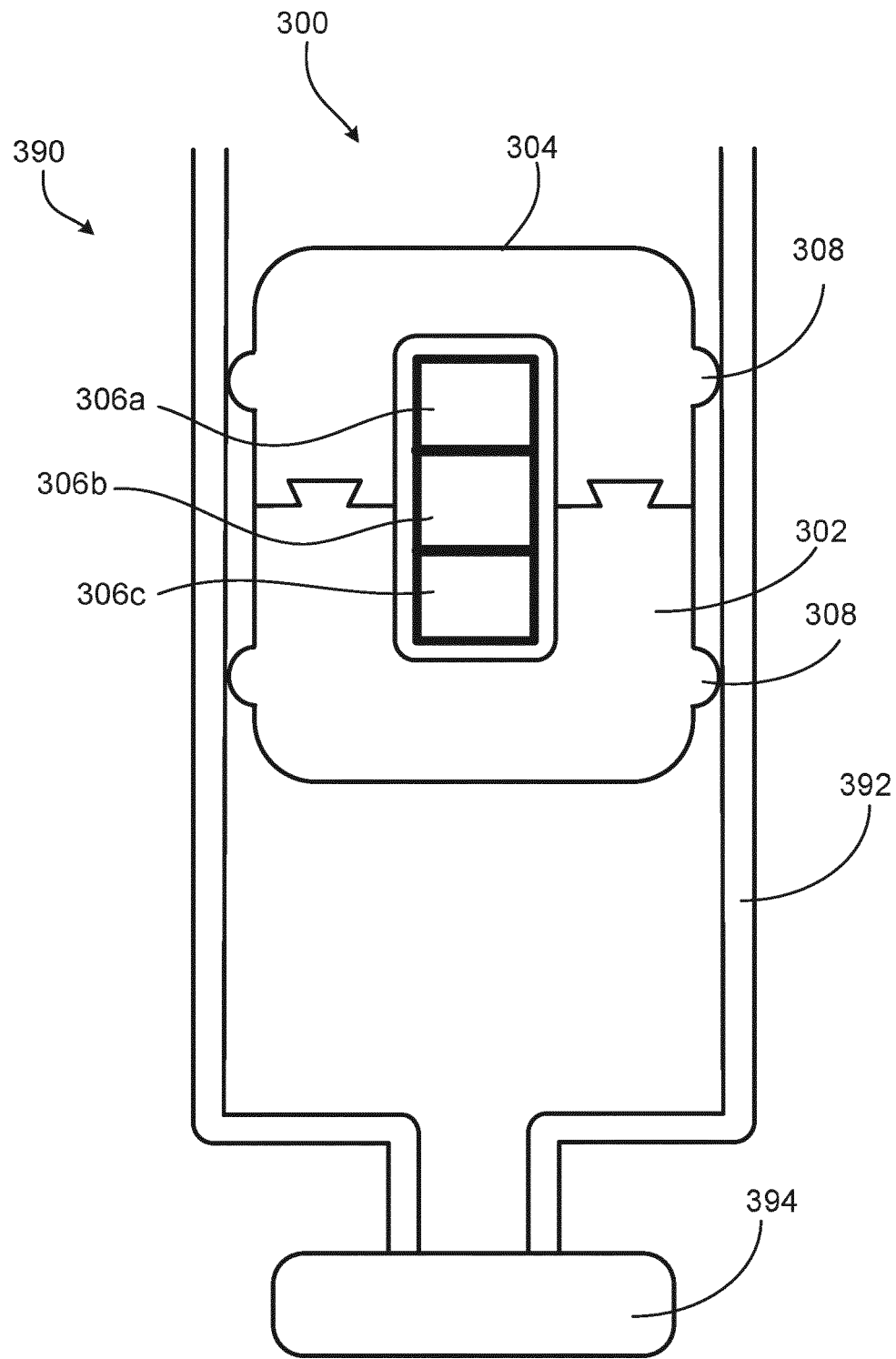
FIG. 3C is a cross sectional view of the plunger of FIGS. 3A and 3B disposed in a cartridge.

FIG. 3C is a cross-sectional view of a plunger disposed within a cartridge 390. The various features of the plunger shown are described above with respect to FIGS. 3A and 3B. The plunger 300 may be replaced by any plunger of the previous figures, which would interface with the cartridge 390 in much the same fashion as will be described here for plunger 300. The cartridge 390 includes a housing 392, which interfaces with the sealing element 308 of the plunger 300 to seal an open end of the cartridge 390. In some instances, a medicament (e.g., a medical fluid or drug) is disposed in the space between the cap 394 of the cartridge 600 and the drug-contacting part 302 of the plunger 300. In some instances, the embedded electronics 306a, 306b, and 306c, include a sensor configured to send and receive a signal to sense a position of the plunger 300 in the cartridge 390.

The sensor 310 may be a sensor/transmitter device such as, for example, a piezoelectric device. A sensor/transmitter may transmit a sensing signal, such as, for example, an ultrasonic, acoustic, light, or other signal through the plunger 300 and measure a response. The response received could be provided to a controller (e.g. an embedded or an external microcontroller) which may receive the response and calculate a state of the cartridge 390. The state of the cartridge 390 may correspond to, for example, a fill level of medicament in the cartridge 390 or a position of the plunger 300. The state of the cartridge may allow measurement of an injected dose of medicament.

The plunger of FIGS. 2A, 2B, 3A, 3B, and 3C may be sterilized, for example, by using a heat sterilization process after the overmolding of the non-drug-contacting part. In an example heat sterilization process, the completed plunger containing the ancillary electronic components would be sterilized at a temperature of approximately 80 to 120 degrees Celsius for between approximately twenty and thirty minutes.

Figure 4A:
FIGS. 4A-4I are illustrations of a technique for manufacturing a two-part plunger with embedded electronics
Figure 4B:
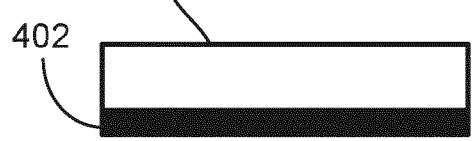

FIGS. 4A-4I are illustrations of a technique for manufacturing a two-part plunger with embedded electronics. FIG. 4A shows a rubber material 401 after mixing and extrusion of the material in a read-to-mold component shape. In some instances, the rubber material 401 includes pharmaceutical-grade thermosets, such as halobutyls, polyisoprenes, and styrene-butadiene. FIG. 4B shows the rubber material 401 after the application of a fluoropolymer film 402 to one side of the rubber material 401 using, for example, a film lamination process. The purpose of this film is to provide a barrier against leaching of unwanted inorganic and organic substances from the plunger to the drug formulation.

Figure 4C:
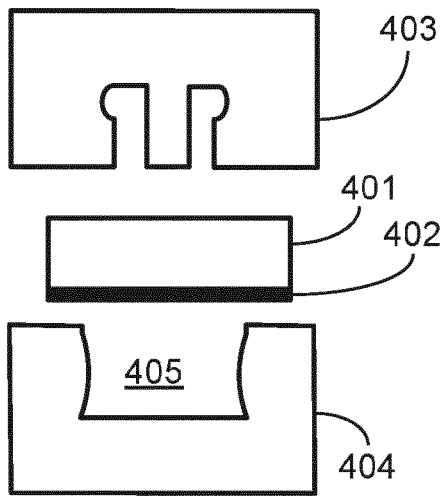
Figure 4D:
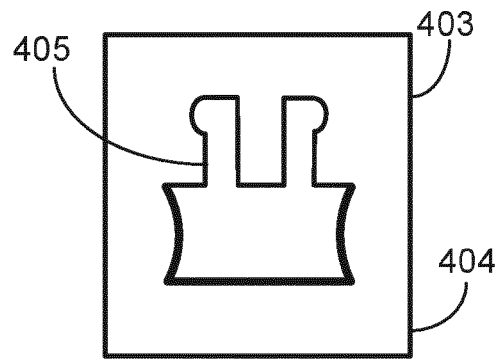

FIG. 4C shows a compression molding apparatus including a top mold 403 and a bottom mold 404, with the laminated rubber material 401 positioned between the top and bottom molds 403, 404. In operation, the top mold 403 and the bottom mold 404 compresses the laminated rubber material 401 into a desired shape of a drug-contacting part 405 of a plunger, as shown in FIG. 4D as a first molding process. The first molding process involves a thermal exposure of the rubber material 401, as defined as the total energy transferred to the material or, more simply, the integral of the temperature of the material over the time of the first molding.

Figure 4E:
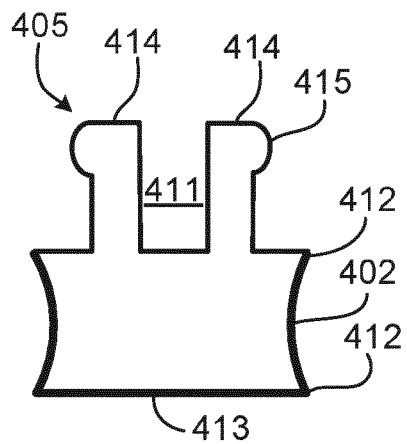

FIG. 4E shows the completed drug-contacting part 405 after the first molding step. The drug-contacting part 405 includes a protrusion 414 forming an inner cavity 411 and a peripheral flange 415 configured to increase the mechanical adhesion of the drug-contacting part 405 to an overmolded part, as described below. The drug-contacting part 405 also defines a bottom surface configured to face the inside of a medicament cartridge and two peripheral sealing edges 412 configured to sealingly interface with an inner surface of the medicament cartridge when inserted. In some instances, the protrusions 414 include geometrical features to allow positioning of an ancillary component in the cavity 411. In some instances, the protrusions 414 include geometrical features to enhance mechanical stability of a part molded over the protrusions 414.

Figure 4F:
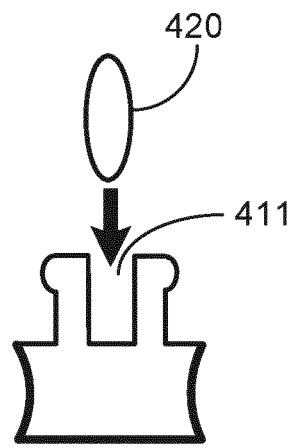
Figure 4G:
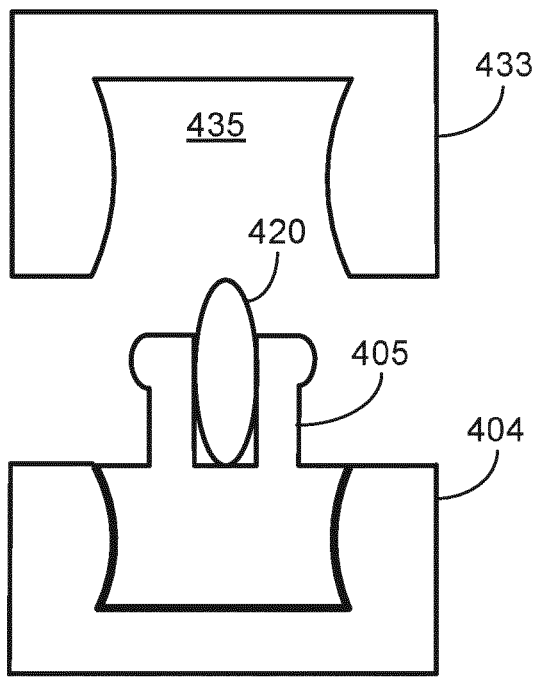

FIG. 4F is an illustration of an ancillary component 420 being inserted into the cavity 411 of the drug-contacting part 405. FIG. 4G shows the drug-contacting part 405 and ancillary component 420 being placed in an injection mold comprising a top mold 433 and a bottom mold 404. In some instances, the bottom mold 404 is the same bottom mold 404 from the first compression molding step, and in other instances the bottom is identical to the bottom mold 404 of the first compression molding step, but the drug-contacting part 405 is removed from the first bottom mold 404 and placed into a new bottom mold of an injection molding machine. FIG. 4G shows the drug-contacting part 405 in the injection molds 404, 433 immediately prior to a material being injected into a cavity 435 of the injection molds 404, 433. In some instances, the injected material is a silicon rubber, which may be, for example, a liquid silicone rubber or high consistency silicone rubber. FIG. 4L shows a completed plunger 440 including the drug-contacting part 405 defining a bottom-half of the plunger 440 with an injection molded non-drug-contacting part 441 surrounding the ancillary component 420 and defining a completed top-half of the plunger 440. The ancillary component 420 is sealed within the plunger 440 between the drug-contacting part 405 and the non-drug-contacting part 441. The non-drug-contacting part includes a top surface 444 configured to be contacted by a head of a plunger rod to drive the plunger 440 into a cartridge. The non-drug-contacting part 441 also includes an exterior peripheral sealing edge 442 forming a third sealing edge of the plunger 440.

In operation, the ancillary components 420 have a thermal budget that may be lower than the thermal exposure of the first compression molding step of FIG. 4D. In some instances, the curing temperature of the drug-contacting part 405 is between 150° C. and 180° C. during the compression molding step. In some instances, the ancillary components have a maximum thermal exposure temperature limit of less than 150° C. In some instances, the injection molding of FIG. 4H includes curing the injected material between 150° C. and 120° C. In some instances, the curing temperature of injected material is lower than 120° C. In some instances, the injected material is lower than 80° C. In some instances, the injected material is lower than 45° C. In some instance, UV exposure can be used to cure the injected material.

In some instances, the maximum thermal exposure limit of the ancillary component 420 is between the temperature of the rubber material 401 during the compression molding and the temperature of the injected material during the injection molding. In some instances, the ancillary component 420 has a thermal budget that defines the maximum thermal energy able to be transferred to the ancillary component 420 before degradation is a concern. In some instances, the temperature of the injected material is above the maximum thermal exposure temperature of the ancillary component 420, but the overall thermal exposure of the injection molding process is less than the thermal budget of the ancillary component 420. That is, the temperature of the injection material is above the maximum temperature threshold for the ancillary component 420, but the total thermal energy transferred to the ancillary component 420 during the injection molding process is less than the thermal budget of the ancillary component 420, and therefore, the ancillary component never reaches it maximum thermal exposure temperature, or, if the ancillary component 420 does, the temperature of the ancillary component 420 does not stay above the maximum temperature long enough for thermal degradation to be a affect the function of the ancillary component 420.

In some instances, the inner cavity 411 of the drug-contacting part 405 is sized to enable the non-drug-contacting part 441 to be formed in the inner cavity 411 without forming a portion surrounding the drug-contacting part 405. In this way, an inner cavity 411 is sized to completely accept the ancillary electronics 420 and the second material is filled into the inner cavity 411 and completely around the ancillary electronics 420, thereby sealing the ancillary electronics 420 into the drug-contacting part 405 and forming the non-drug-contacting part 441 inside the inner cavity 411 using the inner cavity 411 as the mold for the second material instead of the top mold 433. In some instances, forming the non-drug-contacting part 441 includes a deposition process placing the second material on, in, or around the drug-contacting part 405 in a mold-less process.

Figure 5:
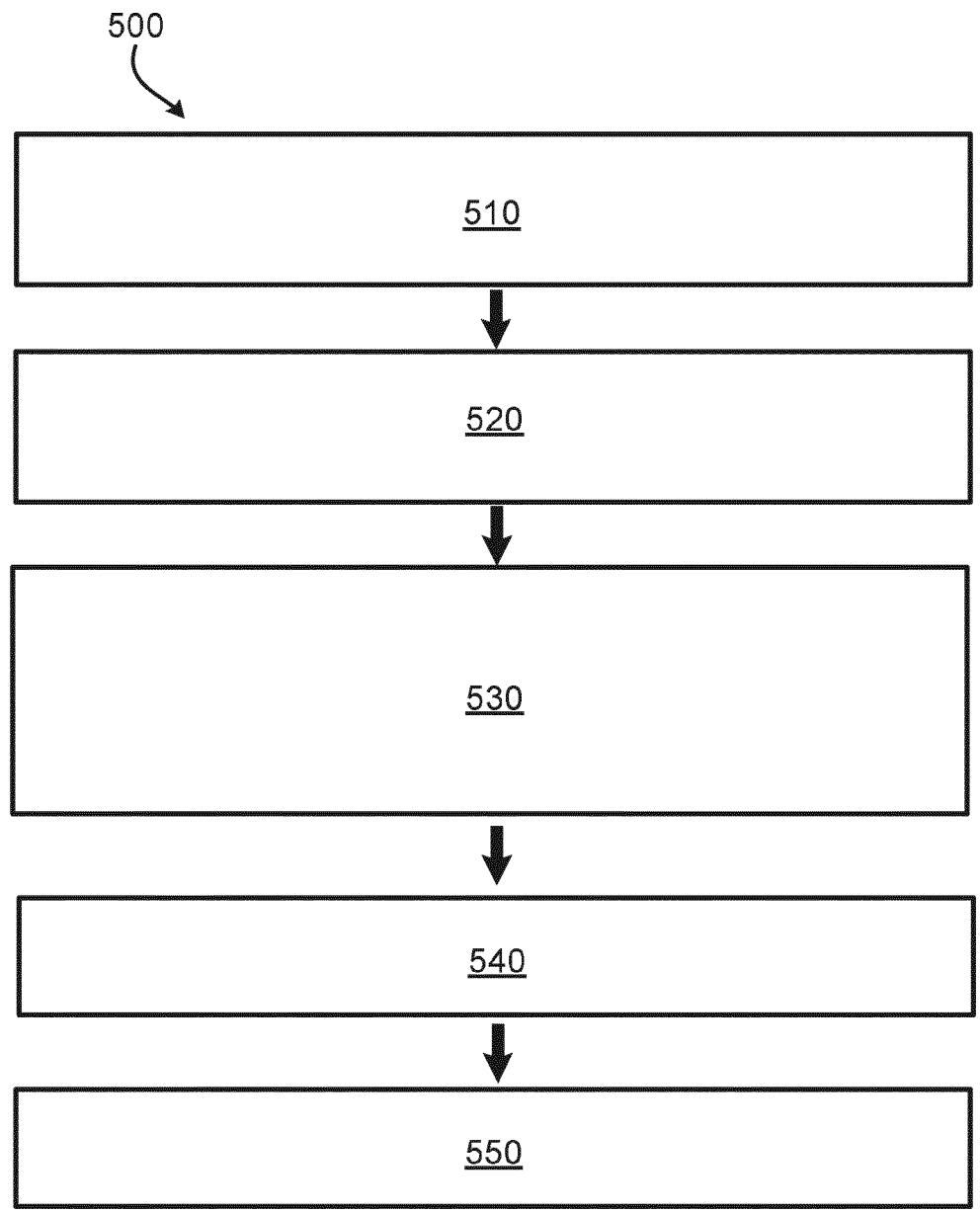
FIG. 5 is a flow chart of a two-part process of molding a plunger with embedded ancillary components using two different materials.

FIG. 5 is a flow chart of a two-part process of molding a plunger with embedded ancillary components using two different materials and different thermal exposures. The multi-step manufacturing process 500 includes molding 510 a drug-contacting part of a container closure (i.e., plunger) with a first material at a first temperature and for a length of time defining a first thermal exposure. This may be done using proven drug contact materials (i.e., halobutyls), potentially with fluoropolymer film lamination and with tradition high-volume compression molding techniques. Next, ancillary components are inserted 520 into the molded drug-contacting part. In some instances, this is done using high-speed pick and place technology, and the inserting 520 can be performed before or after trimming the drug-contacting part. After insertion of the ancillary components, the drug-contacting part and ancillary components are overmolded 530 with a second material at a second temperature and for a length of time defining a second thermal exposure less than a thermal budget of the ancillary components to form a non-drug-contacting part of the container closure. In some instances, the second material is a medical grade material compatible with the thermal budget of the ancillary components, such as, for example, liquid silicone rubber. Additionally, and as explained in more detail below with respect to FIGS. 7-9B, the second material should be compatible with any expected functionally of the ancillary components. Next, the completed plunger (i.e., the drug-contacting part and the non-drug contacting part molded together with the ancillary components embedded inside) is subjected 540 to regular close part processing which, in some instances, includes washing and siliconization. Finally, the completed plunger (i.e., container closure) is sterilized 550 using a technique that exposes the embedded ancillary components to a thermal exposure less than the thermal budget of the ancillary components when embedded in the completed plunger. In some instances, the sterilization process 550 includes Steam, Ethylene Oxide (EtO), Nitrogen Oxide $NO_x$, e-beam, or similar processes known in the art. In some instances, the thermal budget of the ancillary components embedded in the completed plunger is higher than the thermal budget of the ancillary components during the overmolding 530 because the completed plunger may provide a degree of thermal insulation for short-duration sterilization processes.

Figure 6A:
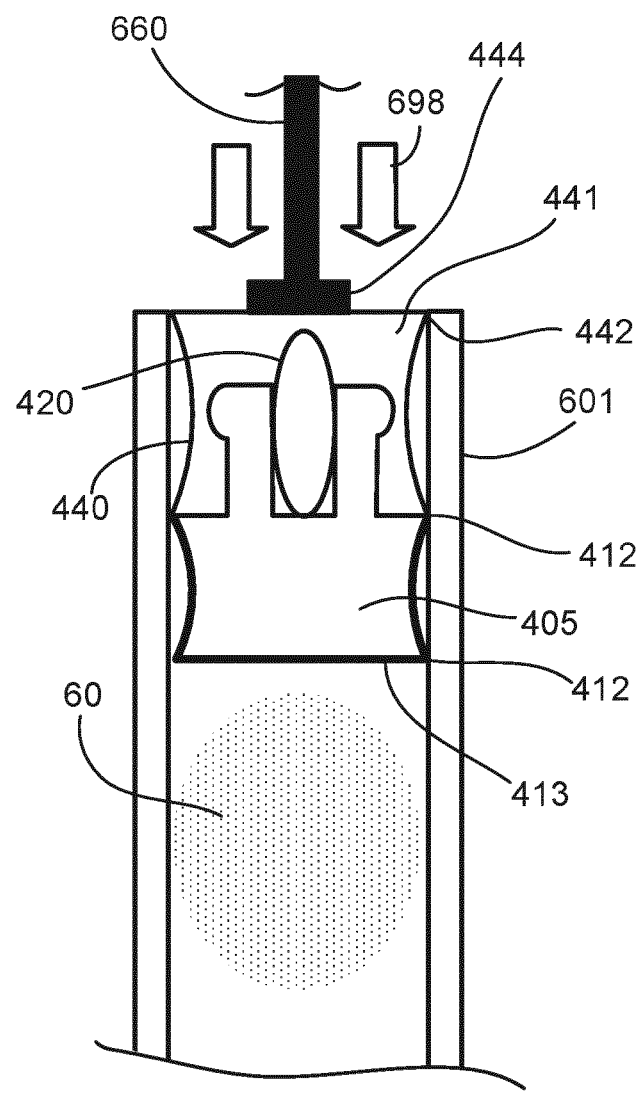
FIG. 6A is cross-sectional view the plunger of FIG. 7A containing the removable insert before being driven by a plunger.

FIG. 6A is cross-sectional view of a plunger 440 disposed within a cartridge 601 and an ancillary electronic component 420 embedded in the plunger 440 between a drug-contacting part 605 and a non-drug-contacting part 441. In some instances, the plunger 440 is an elastomeric container closure. The plunger 440 is shown inside of the cartridge 601, with a plurality of sealing edges 412, 442 of the plunger 440 forming a seal around the bottom surface 413 of the drug-contacting part 405 to contain a medicament 60 in the cartridge 601. In some instances, the ancillary electronic component (or electronic assembly) 420 includes one or more of the following: a sensor, a power source (e.g. battery), a controller, a wireless communication module (e.g. IEEE 802.15, NFC, RF, IrDA), an acoustic module, memory, an on-off switch, a thermo-sensing element, or a pressure sensor. In some instances, ancillary electronic component 420 includes an on-off switch configured to trigger ancillary electronic component 420 by any suitable impact on the non-drug-contacting part 441 of the plunger (e.g. by a force 698 from a plunger rod 660).

FIG. 6A shows the plunger 440 before being driven by a plunger rod 660 into the cartridge 601. The plunger rod 660 (e.g., a plunger rod and head configured to contact the plunger 440) is, in some instances, driven by an actuator or drive mechanism of an injector (as shown in FIG. 1) having the cartridge 601, or is a plunger rod of a syringe where the cartridge 601 is the syringe housing. In operation, the plunger rod 660 is driven (as indicated by arrows 698) against the non-drug-contacting part 441 and thereby applies a force to the plunger drug-contacting part 605 to move the plunger 440 into the cartridge 601 in order to drive a portion of the medicament 60 from the cartridge 601.

Figure 6B:
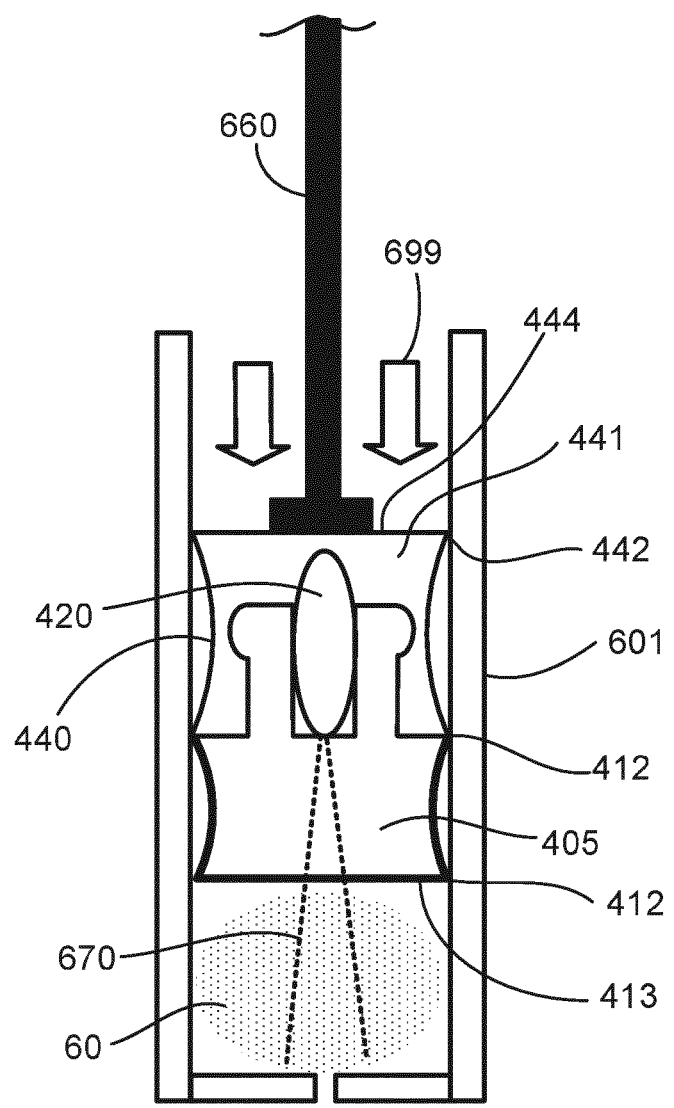
FIG. 6B is cross-sectional view the plunger of FIG. 7B during a sensing operating during or after being driven into the cartridge by the plunger

FIG. 6B is a cross-sectional view the plunger 440 of FIG. 6A during a sensing operating during or after being driven into the cartridge 601 by the plunger rod 660. FIG. 6C shows the plunger rod 660 contacting the non-drug-contacting part 441 of the plunger 440 and having driven the plunger 440 into the cartridge 601 (as shown by arrows 699). In operation, the ancillary electronic component 420 may emit a sensing signal 670, which, in some instances, is responsive to the position of the plunger 440 in the cartridge 601 and enables the ancillary electronic component 420 to generate a signal indication of the movement of the plunger 440.

Some embodiments include a plunger with ancillary electronic components inside disposable medicament injectors such as prefilled single and double chamber syringes. The examples described above for integrating ancillary components into the plunger of a cartridge can be extended from the use in cartridges to disposable prefilled syringes. Additionally, in some instances, in a dual chamber syringe or cartridge, aspects detailed herein are disposed in a middle plunger to sense and/or measure the status of the device (e.g., "pre mixing", "mixed solution ready," or "injected completed" based on the sensing signal).

Described below are devices and techniques for providing energy to electronic circuity in cartridge systems (for example, those disclosed herein) using energy harvesting to provide an alternative to standard batteries or as a supplement to batteries.

Aspects of the systems disclose above enable medical injectors to employ 'smart' technologies by way of an attached embedded electronic component (e.g. RFID, sensor) to provide certain functionality to a cartridge of an injector device (e.g. of a pen-type injector). When integrating electronics into the plunger of a cartridge, one or more components may be active (e.g., a sensor to measure certain properties of the injector or cartridge) and require an energy source, which typically could be a battery. Alternative, as described below, is to use different means of energy harvesting as alternative to a battery.

Figure 7:
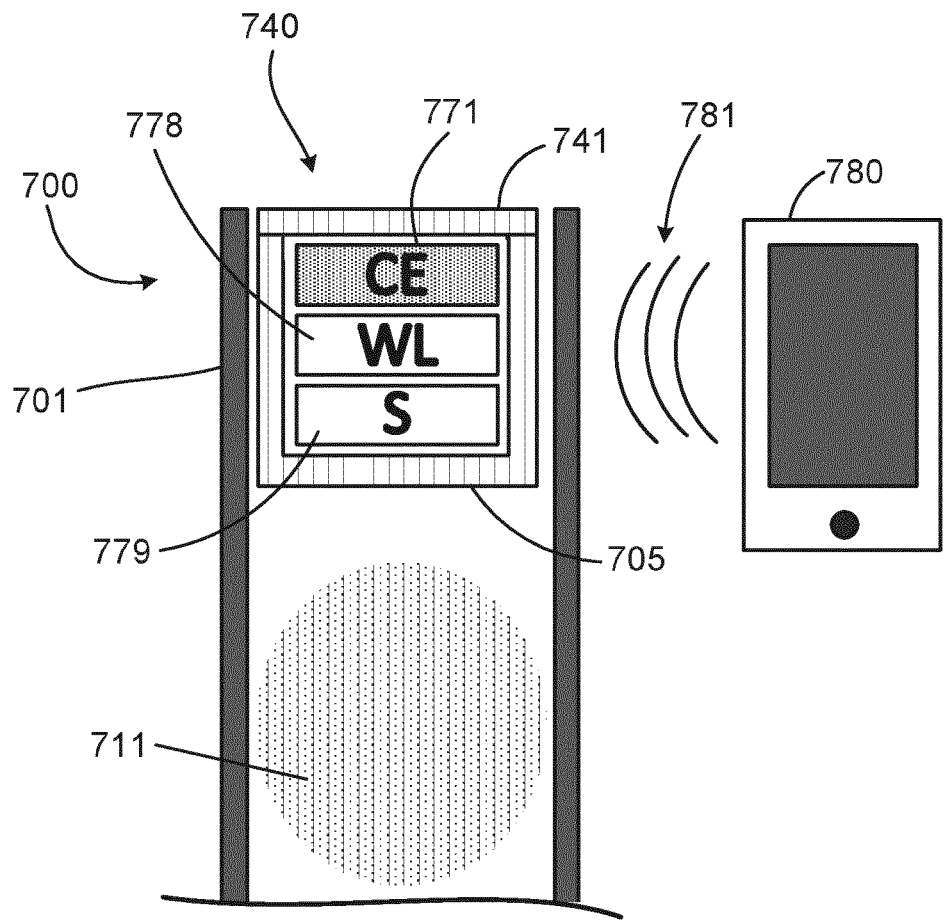
FIG. 7 is cross-sectional view of a plunger disposed within a cartridge and powered by a wireless system.

FIG. 7 is a cross-sectional view of a plunger 740 disposed within a cartridge 700 and powered by a wireless system 780. One example of an energy harvesting system is shown in FIG. 7. FIG. 7 shows a cartridge 700 including a plunger 740 disposed in a housing 701 of the cartridge 700. The plunger 740 includes a drug-contacting part 705, which seals a medicament 711 in the housing 701. The plunger 740 also includes a non-drug-contacting part 741 sealing ancillary electronic components 771, 778, 779 into the plunger 740. The ancillary electronic components 771, 778, 779 include a sensing device (S) 779, a wireless device (WL) 778, and a capacitive device (CE) 771.

In operation, the sensing device 779 is configured to sense the position of the plunger 740 within the housing 701, and the wireless device 778 is configured to communicate with an external electronic device (not shown) in order to communicate information from the sensor device 779. The capacitive device 771 is configured to provide electric power to the sensing device 779 and the wireless device 778 by way of wireless inductive charging from a wireless signal 781 located in proximity to the cartridge 700. In some instances, the capacitive device 771 includes capacitive circuitry that is configured receive power wirelessly from, for example, a wireless system 780 (e.g., a smartphone) via a nearfield communication protocol (NFC) signal 781, or by a typical wireless charging device with other means of inductive loading, in order to provide enough energy for initiating and performing measurements with the sensing device 779 in the cartridge 700 and for transmitting back the results using the wireless device 778.

FIGS. 8A and 8B are cross-sectional views of a plunger disposed within a cartridge and powered by a piezoelectric system. Another example of an energy harvesting system is the use of a piezo technology to collect energy from the mechanical forces occurring in between the plunger rod and plunger during, for example, injector handling or an injection operation, to provide enough energy for initiating and performing the measurement in the cartridge and for transmitting back the results. FIG. 8A shows a cartridge 800 having a plunger 840 disposed in a housing 801 of the cartridge 800 and a plunger rod 860 advancing (e.g., along arrow 897) to contact a non-drug-contacting part 810 of the plunger 840. A drug-contacting part 805 of the plunger 840 seals a medicament 811 in the housing 801 by being sealingly engaged to an inner surface of the housing 801. The non-drug-contacting part 810 is molded over ancillary electronic components 872, 878, 879 inserted into the drug-contacting part 805 of the plunger, and the non-drug-contacting part 810 is configured to at least partially deflect under the force of the plunger rod 860 or otherwise enable a transfer for force from the plunger to a portion of the ancillary electronic components 872, 878, 879. The ancillary electronic components 872, 878, 879 include a sensing device (S) 879, a wireless device (WL) 878, and a piezoelectric element (PE) 872.

In operation, the sensing device 879 is configured to sense the position of the plunger 840 within the housing 801, and the wireless device 878 is configured to communicate with an external electronic device (not shown) in order to communicate information from the sensor device 879. The piezoelectric element 872 is configured to provide electric power to the sensing device 879 and the wireless device 878 by way of transforming a portion of the force applied to the plunger 802 into electric energy. As shown in FIG. 8B, the piezoelectric element 872 is transformed from a position 898 of FIG. 8A to a deflected position 899 of FIG. 8B by the force applied to the non-drug-contacting part 810 by the plunger rod 860 (during the motion indicated by arrow 897). The transformation of the piezoelectric element 872 from position 898 to the deflected position 899 absorbs energy and converts a portion of it to electric energy.

FIGS. 9A and 9B are cross-sectional views of a plunger disposed within a cartridge and including a Peltier thermoelectric device. Another example of an integrated energy harvesting device is the inclusion of Peltier elements (PE) to convert the temperature differences between refrigeration (e.g., of the pen or injector during storage) and warming (e.g., exposure to room temperatures) into electric energy to provide enough energy for initiating and performing the measurement in a cartridge of the injector/pen and for transmitting back the results. FIG. 9A shows a cartridge 900 being stored in a low temperature environment (e.g., 4° C.) and having a plunger 940 disposed in a housing 901 of the cartridge 900 and plunger rod 860 positioned against a non-drug-contacting part 941 of the plunger 940. A drug-contacting part 405 of the plunger 940 sealingly contains a medicament 911 in the housing 901 by being sealingly engaged to an inner surface of the housing 901. The non-drug-contacting part 941 surrounds embedded ancillary electronic components 973, 978, 979, and the non-drug-contacting part 941 or plunger 902 is configured to at least partially transfer thermal energy to the ancillary electronic components 973, 978, 979. The ancillary electronic components 973, 978, 979 include a sensing device (S) 979, a wireless device (WL) 978, and a thermoelectric element (TE) 973.

In operation, the sensing device 979 is, in some instances, configured to sense the position of the plunger 940 within the housing 901, and the wireless device 978 is configured to communicate with an external electronic device (not shown) in order to communicate information from the sensor device 979. The thermoelectric element 973 is configured to provide electric power to the sensing device 979 and the wireless device 978 by way of generating energy when the temperature of the thermoelectric element changes. As shown in FIG. 9B, the cartridge 900 is moved to a relatively higher temperature environment (e.g., 20° C.) and the thermoelectric element 973 is heated by absorbing thermal energy from the environment outside the cartridge 900 (during the temperature transition indicated by arrow 999). The absorption of thermal energy by the thermoelectric element 973 generates electric energy to power, for example, the sensing device 979 and the wireless device 978.

Some of the features described can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a volume of a drug into a human or animal body. The volume can typically range from about 0.5 ml to about 10 ml. Without limitation, the drug delivery device may include a syringe, needle safety system, pen injector, auto injector, large-volume device (LVD), pump, perfusion system, or other device configured for subcutaneous, intramuscular, or intravascular delivery of the drug.

Such devices often include a needle, wherein the needle can include a small gauge needle (e.g., greater than about 24 gauge, and including 27, 29, or 31 gauge).

In combination with a specific drug, the presently described devices may also be customized in order to operate within required parameters. For example, within a certain time period (e.g., about 3 to about 20 seconds for injectors, and about 5 minutes to about 60 minutes for an LVD), with a low or minimal level of discomfort, or within certain conditions related to human factors, shelf-life, expiry, biocompatibility, environmental considerations, etc. Such variations can arise due to various factors, such as, for example, a drug ranging in viscosity from about 3 cP to about 50 cP.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively, or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin; B29-N-(N-lithocholyl-gamma-glutamyl)-des(B30) human insulin; B29-N-(w-carboxyheptadecanoyl)-des(B30) human insulin and B29-N-(w-carboxyheptadecanoyl) human insulin.

Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (such as, for example, adjustments, additions, or removals) of various components of the substances, formulations, apparatuses, methods, systems, devices, and embodiments described herein may be made without departing from the full scope and spirit of the present inventive concepts, which encompass such modifications and any equivalents thereof.

A number of implementations of the present disclosure have been described. Nevertheless, it will be understood that various modifications may be made without departing from the spirit and scope of the present disclosure. Accordingly, other implementations are within the scope of the following claims.

A number of implementations of the present disclosure have been described. Nevertheless, it will be understood that various modifications may be made without departing from the spirit and scope of the present disclosure. Accordingly, other implementations are within the scope of the following claims.

The invention claimed is:

1. A method of manufacturing an elastomeric container closure with embedded functional components, the method comprising:
    molding a drug-contacting part of the elastomeric container closure from a first material at a first temperature and for a first length of time, the exposure of the first material to the first temperature for the first length of time defining a first thermal exposure;
    after molding the drug-contacting part, inserting electronic components into the drug-contacting part, the electronic components having an operational thermal budget less than the first thermal exposure; and
    depositing a second material on the drug-contacting part and the inserted electronic components to form the elastomeric container closure, wherein forming the elastomeric container closure includes overmolding a non-drug-contacting part around the drug-contacting part with the second material at a second temperature for a second length of time to seal the electronic components inside the elastomeric container closure, the non-drug-contacting part shaped and sized to contact a sidewall of a medicament container when the elastomeric container closure is disposed in the medicament container, the exposure of the second material to the second temperature for the second length of time defining a second thermal exposure that is less than the operational thermal budget of the electronic components.

2. The method of claim 1, wherein the electronic components are configured to operate after exposure to temperatures lower than the first temperature of the first material during the molding step.

3. The method of claim 2, wherein the second temperature is lower than the first temperature, and where the electronic components are configured to operate after exposure to the second temperature of the second material during the overmolding step.

4. The method of claim 3, wherein the electronic components are incompatible with the first temperature of the molding of the drug-contacting part.

5. The method of claim 1, wherein the first material comprises halobutyls.

6. The method of claim 1, wherein the second material comprises silicone rubber.

7. The method of claim 1, wherein molding the drug-contacting part comprises molding the drug-contacting part in a first mold, and wherein overmolding comprises overmolding the non-drug-contacting part around the drug-contacting-part and the electronic components with the second material in a second mold.

8. The method of claim 7, comprising removing the drug-contacting part from the first mold and disposing the drug-contacting part into the second mold prior to the overmolding.

9. The method of claim 1, wherein molding the drug-contacting part comprises compressing the drug-contacting part such that the shape of the drug-contacting part comprises a peripheral flange configured to increase mechanical adhesion of the drug-contacting part to the overmolded non-drug-contacting part.

10. The method of claim 1, wherein forming the non-drug contacting part comprises a deposition process for placing the second material on, in, or around the drug-contacting part.

11. The method of claim 10, wherein the deposition process comprises an ultraviolet (UV) curing process of the second material.

12. The method of claim 1, wherein the second temperature is between 60° C. and 120° C.

13. The method of claim 1, wherein the drug-contacting part is shaped and sized to contact the sidewall of the medicament container when the elastomeric container closure is disposed in the medicament container.

14. The method of claim 1, wherein at least a portion of the electronic components extends axially into the non-drug-contacting part.

15. The method of claim 1, wherein an axial length of the non-drug-contacting part is substantially the same as, or greater than, an axial length of the drug-contacting part.

16. The method of claim 1, wherein the non-drug-contacting part comprises a first seal for sealing against the sidewall of the medicament container when the elastomeric container closure is disposed in the medicament container.

17. The method of claim 16, wherein the first seal is integrally formed with the non-drug-contacting part.

18. The method of claim 16, wherein the drug-contacting part comprises a second seal for sealing against the sidewall of the medicament container when the elastomeric container closure is disposed in the medicament container.

19. A method of manufacturing an elastomeric container containing electronic components, the method comprising:
   molding a first part of the elastomeric container using a first thermal energy that exceeds an operational thermal energy limit of the electronic components, the first part configured to contact a medicament of a medicament container when the elastomeric container is disposed in the medicament container;
   after molding the first part, inserting the electronic components into the first part; and
   after inserting the electronic components into the first part, overmolding a second part on the first part and the electronic components using a second thermal energy that does not exceed the operational thermal energy limit of the electronic components, the second part shaped and sized to contact a sidewall of the medicament container when the elastomeric container is disposed in the medicament container.

20. The method of claim 19, wherein an axial length of the second part is substantially the same as, or greater than, an axial length of the first part.

21. The method of claim 19, wherein the second part comprises a seal for sealing against the sidewall of the medicament container when the elastomeric container is disposed in the medicament container.

* * * * *

UNITED STATES PATENT AND TRADEMARK OFFICE
CERTIFICATE OF CORRECTION

PATENT NO. : 11,975,464 B2
APPLICATION NO. : 16/954335
DATED : May 7, 2024
INVENTOR(S) : Paolo Mangiagalli Page 1 of 1

It is certified that error appears in the above-identified patent and that said Letters Patent is hereby corrected as shown below:

In the Specification

Figure 4H:
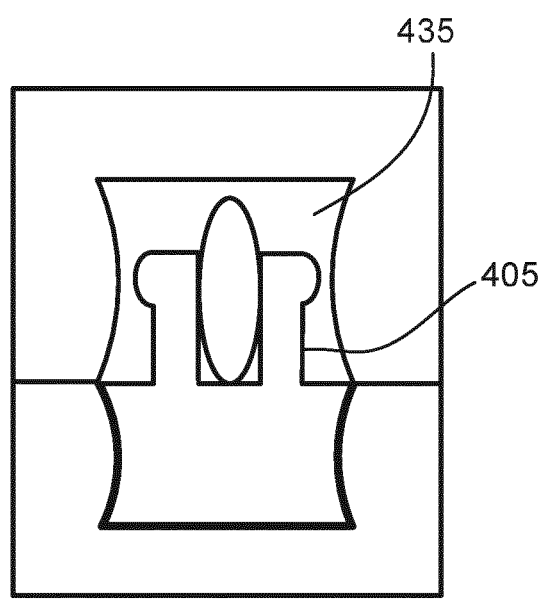
Figure 4I:
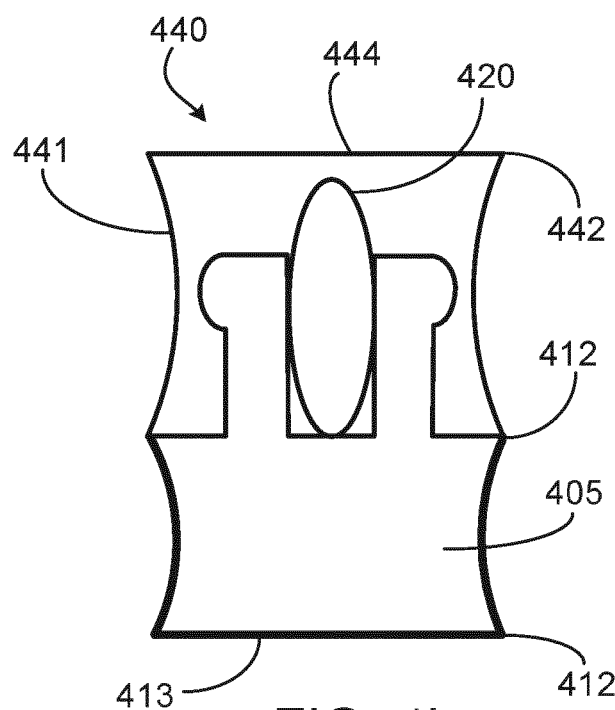

Column 4, Line 8, delete "FIG. 7A" and insert -- FIG. 4I --

Column 4, Line 11, delete "FIG. 7B" and insert -- FIG. 4I --

Column 9, Line 39, delete "FIG. 4G" and insert -- FIG. 4H --

Column 9, Line 44, delete "FIG. 4L" and insert -- FIG 4I --

Column 11, Line 54, delete "FIG. 6C" and insert -- FIG. 6B --

Signed and Sealed this
Twenty-fifth Day of March, 2025

Coke Morgan Stewart
*Acting Director of the United States Patent and Trademark Office*